United States Patent
Tenn, III

(10) Patent No.: US 10,640,459 B2
(45) Date of Patent: May 5, 2020

(54) INHIBITING CPI FORMATION FROM ADIPONITRILE

(71) Applicant: INVISTA NORTH AMERICA S.A R.L., Wilmington, DE (US)

(72) Inventor: William J. Tenn, III, Beaumont, TX (US)

(73) Assignee: INVISTA North America S.a.r.l., Wilmington, DE (US)

( * ) Notice: Subject to any disclaimer, the term of this patent is extended or adjusted under 35 U.S.C. 154(b) by 0 days.

(21) Appl. No.: 15/755,235

(22) PCT Filed: Aug. 31, 2016

(86) PCT No.: PCT/US2016/049582
§ 371 (c)(1),
(2) Date: Feb. 26, 2018

(87) PCT Pub. No.: WO2017/040583
PCT Pub. Date: Mar. 9, 2017

(65) Prior Publication Data
US 2018/0244607 A1    Aug. 30, 2018

Related U.S. Application Data

(60) Provisional application No. 62/305,329, filed on Mar. 8, 2016, provisional application No. 62/213,678, filed on Sep. 3, 2015.

(51) Int. Cl.
*C07C 253/34* (2006.01)
*B01D 3/14* (2006.01)
*B01D 3/34* (2006.01)

(52) U.S. Cl.
CPC ........... *C07C 253/34* (2013.01); *B01D 3/143* (2013.01); *B01D 3/34* (2013.01)

(58) Field of Classification Search
CPC .......... C07C 253/34; B01D 3/143; B01D 3/34
See application file for complete search history.

(56) References Cited

U.S. PATENT DOCUMENTS 3,496,212 A    2/1970 Davison et al.
3,758,545 A    9/1973 Pounder et al.
(Continued)

FOREIGN PATENT DOCUMENTS

CA    672712 A    10/1963
CA    1043813    12/1978
(Continued)

OTHER PUBLICATIONS

International Search Report and Written Opinion Received for PCT Patent Application No. PCT/US2016/049582, dated Oct. 31, 2016, 8 pages.
(Continued)

*Primary Examiner* — Brian A McCaig
(74) *Attorney, Agent, or Firm* — Invista North America S.A.R.L.

(57) ABSTRACT

Disclosed is a method for inhibiting the formation of by-products from dinitriles, such as the formation of cyclopentylideneimine (CPI) from Adiponitrile (ADN), comprising adding an effective amount of a Brønsted acid to the ADN. Also disclosed is a method of refining a dinitrile compound by distillation the method comprising the steps of: (a) supplying (i) a feedstream comprising the dinitrile compound and (ii) a Brønsted acid to a distillation apparatus; and (b) withdrawing from the distillation apparatus an overhead distillate stream comprising the dinitrile compound.

13 Claims, 3 Drawing Sheets

(56) References Cited

U.S. PATENT DOCUMENTS

| | | | |
|---|---|---|---|
| 3,775,258 A | 11/1973 | Kershaw | |
| 6,599,398 B1 | 7/2003 | Ostermaier et al. | |
| 2008/0083607 A1* | 4/2008 | Deckert | B01D 11/0434 203/43 |
| 2016/0376227 A1* | 12/2016 | Luyken | C07C 209/48 558/456 |

FOREIGN PATENT DOCUMENTS

| | | | | |
|---|---|---|---|---|
| GB | 1094908 | | 12/1967 | |
| WO | WO 2015/117933 | * | 8/2015 | ........... C07C 253/34 |
| WO | 2017/040583 A1 | | 3/2017 | |

OTHER PUBLICATIONS

International Preliminary Report on Patentability Received for PCT Patent Application No. PCT/US2016/049582, dated Mar. 15, 2018, 7 pages.

\* cited by examiner

INHIBITING CPI FORMATION FROM ADIPONITRILE

BACKGROUND

Dinitrile compounds, such as adiponitrile (ADN), are important commercial chemicals. The most important application of dinitriles being as intermediates in the production of diamine monomers, which are useful in the synthesis of various polyamide polymers. The hydrogenation of ADN provides hexamethylenediamine (HMD), which is one of the essential ingredients used to manufacture nylon 66 (N66). N66 is produced by reacting HMD with adipic acid (AA) to form an aqueous salt solution. This salt solution is then heated to remove the solvent water, and subsequently to react the amine end of the HMD with the acid end of the AA to produce an amide linkage and a molecule of water. This reaction is known as a condensation polymerization because it produces a molecule of water for each amide linkage formed. The formation of multiple amide linkages leads to the formation of the N66 polymer. The N66 polymer can be used to produce synthetic fibers and engineering polymers which are of great commercial value.

In order to produce high quality polyamides, the essential ingredients must be of extremely high purity. The presence of impurities causes weakening of the fiber and undesirable color of the polymer. Undesirable impurities in the diamines are removed primarily by distillation operations, while impurities in dicarboxylic acids such as AA are removed primarily by crystallization. Some of the impurities in the diamines are produced during the hydrogenation of dinitriles, and would exist even if the dinitriles were absolutely pure. Other impurities in the diamines result from the presence of impurities that are contained in the dinitriles, in particular impurities that are formed by unwanted side reactions of dinitriles during dinitriles production and refining. One of the most detrimental impurities to N66 quality is 2-aminomethylcyclopentylamine (AMC), which is formed primarily by the hydrogenation of the impurity 2-cyanocyclopentylideneimine (CPI) that is formed via the cyclization of ADN.

The removal of CPI from ADN is difficult, as the relative volatility of CPI to ADN is 1.45. However, the removal of AMC from HMD is much more difficult, as the relative volatility of AMC to HMD is 1.20. Thus, to maintain low levels of AMC in the HMD product, it is best to remove the CPI from the ADN prior to hydrogenation.

The presence of CPI in ADN has been a major problem from the first days of ADN manufacture. While there have been several processes for making ADN, they all have had to deal with the CPI problem. The primary method for removing CPI from ADN is vacuum distillation, but when sufficiently low levels of CPI cannot be achieved, other options have been employed to remove the CPI after distillation. U.S. Pat. No. 3,496,212 describes the use of a water soluble aldehyde in combination with an extraction step using an aromatic solvent and water followed by an additional distillation step. Canadian patent 672,712 employs ozone treatment of the ADN to destroy the CPI. U.S. Pat. No. 3,758,545 uses paraformaldehyde to chemically react with the CPI. U.S. Pat. No. 3,775,258 hydrolyzes the CPI to the ketone using an acidic catalyst at 140° C. Canadian patent 1,043,813 uses a weak cation exchange resin to remove the CPI from the ADN. All of these processes are directed to the removal of CPI from the ADN. A far better approach would be to prevent the formation of the CPI during the ADN manufacturing process.

One of the leading commercial process for producing ADN is the hydrocyanation of 1,3-butadiene to 3-pentenenitrile (3PN), followed by the hydrocyanation of the 3PN to ADN. These hydrocyanations are performed using a nickel (0) catalyst stabilized with phosphite ligands. These phosphite ligands can be either monodentate or bidentate. The hydrocyanation of 3PN also requires the use of a Lewis acid co-catalyst. When using a bidentate ligand catalyst system, zinc chloride ($ZnCl_2$) is a suitable Lewis acid. One of the advantages of the direct hydrocyanation process is the hydrocyanation of 3PN takes place at mild temperature conditions where virtually no CPI is generated. However, in order to refine the crude ADN to the high purity product required for hydrogenation to HMD, several distillation steps are required. Because of the very low vapor pressure of ADN, these distillations involve temperatures as high as 200° C. At these high temperatures CPI generation occurs during these distillation operations.

There is therefore a need in the art for processes for the preparation of dintriles, such as ADN, of high purity in which the formation of byproducts such as CPI is suppressed. It has now been identified that the addition of a Brønsted acid to dinitriles suppresses side reactions of the dinitriles which can lead to the formation of unwanted by-products, such as the formation of CPI from ADN.

SUMMARY

In a first aspect, the present disclosure provides a method of refining a dinitrile compound the method comprising the steps of:

(a) supplying (i) a feedstream comprising the dinitrile compound and (ii) a Brønsted acid to a distillation apparatus; and (b) withdrawing from the distillation apparatus an overhead distillate stream comprising the dinitrile compound.

It has been found that the presence of a Brønsted acid in the distillation of dinitrile compounds can significantly reduce the amount of by-products formed by side-reactions of the dinitrile compounds during distillation. It is preferred that the dinitrile product is separated from the Brønsted acid during the distillation, i.e., such that the Brønsted acid is withdrawn from the distillation apparatus in a bottoms stream along with other impurities from the dinitrile-containing feedstream. The Brønsted acid may optionally be recycled, suitably following one or more Brønsted acid purification steps.

The dinitrile compound is preferably selected from dinitrile compounds of the formula (I):

$$NC—R^1—CN \qquad (I)$$

wherein $R^1$ represents a $C_1$ to $C_{10}$ straight chain or branched alkylene group. Preferably, $R^1$ represents a $C_2$ to $C_8$ straight chain or branched alkylene group, more preferably $R^1$ represents a $C_2$ to $C_6$ straight chain or branched alkylene group, still more preferably $R^1$ represents a $C_2$ to $C_4$ straight chain or branched alkylene group, and most preferably $R^1$ represents a $C_4$ straight chain or branched alkylene group. For example the dinitrile compound of formula (I) may be selected from ADN and 2-methylglutaronitrile (NC—CH($CH_3$)($CH_2$)$_2$—CN). Most preferably, the dinitrile compound of formula (I) is ADN.

It is believed that the formation of unwanted by-products during the distillation of dinitrile compounds is due at least in part to the presence of Lewis acids in the dinitrile-containing feedstream. Lewis acids may be present for example as co-catalysts used in the hydrocyanation of unsaturated mononitriles to dinitriles, such as the hydrocyanation of 3PN to form ADN. Thus, the feedstream to the distillation in step (a) may comprise a Lewis acid. Lewis acids may be selected from $ZnX_2$, $BX_3$ and $AlX_3$, wherein X represents a halogen, trifluoromethanesulfonate, methanesulfonate or toluenesulfonate. In particular, the feedstream to the distillation apparatus in step (a) may comprise a Lewis acid selected from $ZnCl_2$, $BCl_3$ or $AlCl_3$.

The amount of Lewis acid present in the dinitrile-containing feedstream may suitably be in the range of from 50 to 10,000 ppm (by weight) based on the total weight of the dinitrile-containing feedstream, for example, the amount of Lewis acid present may be from 100 to 5,000 ppm, from 200 to 2,000 ppm, from 200 to 1,500 ppm or from 300 to 1,000 ppm based on the total weight of the dinitrile-containing feedstream.

The feedstream to the distillation apparatus in step (a) may suitably comprise a reaction effluent from a process for the production of dinitriles via the hydrocyanation of unsaturated mononitriles. In particular, the feedstream to the distillation apparatus in step (a) may comprise a reaction effluent from a process from the production of ADN via the hydrocyanation of 3PN. Such reaction effluents may comprise a Lewis acid as described above and/or a hydrocyanation catalyst, such as a nickel (0) catalyst stabilized with phosphorus-containing ligands (such as mono- or bi-dentate phosphite ligands) and/or excess phosphorus-containing ligands. Suitably, the Lewis acid, hydrocyanation catalyst, and any excess phosphorus-containing ligands are recovered from the distillation in a bottoms stream, which also preferably comprises the Brønsted acid.

The Brønsted acid is suitably selected from Brønsted acids having low volatility such that the dinitrile may be separated from the Brønsted acid in a distillate stream, the Brønsted acid being recovered from the distillation apparatus in a bottoms stream. Preferably, the Brønsted acid is thermally stable, such that it does not degrade under conditions for distillation of the dinitrile compound. Examples of suitable Brønsted acids include phosphoric acids (including $H_3PO_4$, polyphosphoric acids and pyrophosphoric acid), sulfuric acid and low volatility sulfonic acids, including $C_4$ to $C_{12}$ alkanesulfonic acids and $C_7$ to $C_{18}$ alkylbenzenesulfonic acids. Examples of suitable octanesulfonic acid, decanesulfonic acid, dodecanesulfonic acid, 4-toluenesulfonic acid, 4-ethylbenzenesulfonic acid, 4-butylbenzenesulfonic acid and 4-dodecylbenzenesulfonic acid. A preferred sulfonic acid is 4-dodecylbezenesulfonic acid.

The Brønsted acid is preferably supplied to the distillation apparatus in an amount of from 5 to 5,000 ppm by weight, based on the total weight of the dinitrile-containing feedstream and the Brønsted acid. For example, the Brønsted acid may be supplied to the distillation apparatus in an amount of from 5 to 1,000 ppm by weight, 10 to 500 ppm by weight, 50 to 400 ppm by weight, or 100 to 250 ppm by weight based on the total weight of the dinitrile-containing feedstream and the Brønsted acid.

The distillation apparatus is suitably operated at subatmospheric pressure with a bottom temperature in the range of from 20 to 300° C., more preferably in the range of from 50 to 250° C., more preferably from 80 to 200° C. In the case of adiponitrile, the distillation apparatus is still more preferably operated with a bottom temperature in the range of from 100 to 200° C., more preferably 120 to 200° C. and most preferably from 150 to 200° C.

The distillation apparatus may comprise a single distillation column or a plurality of distillation columns. In the case that the distillation apparatus comprises a plurality of distillation columns, the Brønsted acid is supplied to at least one of the distillation columns. More preferably, the Brønsted acid is supplied to each of the distillation columns.

In a second aspect, the disclosure provides a method for inhibiting the formation of by-products from a dinitrile compound, the method comprising adding an effective amount of a Brønsted acid to the dinitrile compound.

The dinitrile compound of formula (I) may suitably be selected from any of the dinitrile compounds of formula (I) described above. In a preferred embodiment, this aspect of the disclosure is directed to a method for inhibiting the formation of 2-cyclopentylideneimine (CPI) from adiponitrile (ADN) comprising adding an effective amount of a Brønsted acid to the ADN. Suitably, the Brønsted acid is not vaporized in the presence of the dinitrile compound of formula (I).

The method of the second aspect may comprise the refining of dinitrile compounds by distillation wherein (i) a feedstream comprising a dinitrile compound and (ii) the Brønsted acid are supplied to a distillation apparatus; and an overhead distillate stream comprising the dinitrile compound is withdrawn from the distillation apparatus.

The method suitably comprises separating the dinitrile compound from the Brønsted acid by distillation, i.e., wherein the distillation conditions are controlled such that the Brønsted acid is not vaporized. Suitably, the Brønsted acid has low volatility, such that the dinitrile may be separated from the Brønsted acid in a distillate stream, the Brønsted acid being recovered from the distillation apparatus in a bottoms stream along with other impurities separated from the dinitrile during the distillation. Examples of suitable Brønsted acids in accordance with the second aspect of the disclosure are as described above. The Brønsted acid can optionally be purified and recycled.

The dinitrile compound may be in admixture with a Lewis acid as described above. Where the method of the second aspect of the disclosure comprises the refining of dinitrile compounds by distillation, the Lewis acid may suitably be separated from the dinitrile compound during the distillation, preferably wherein the Lewis acid is recovered from the distillation apparatus in a bottoms stream that may also comprise the Brønsted acid.

The method of the second aspect of the disclosure may suitably comprise the distillation of a reaction effluent from a process for the production of dinitriles via the hydrocyanation of unsaturated mononitriles, such as the distillation of a reaction effluent from a process from the production of ADN via the hydrocyanation of 3PN. Such reaction effluents may comprise a Lewis acid as described above and/or a hydrocyanation catalyst, such as a nickel (0) catalyst stabilized with phosphorus-containing ligands (such as mono- or bi-dentate phosphite ligands) and/or excess phosphorus-containing ligands. Suitably, the Lewis acid, hydrocyanation catalyst, and any excess phosphorus-containing ligands are recovered in a bottoms stream, preferably that also comprises the Brønsted acid.

As used herein, the term "effective amount" when referring to a Brønsted acid means a detectable amount of a Brønsted acid that, when added to a dinitrile-containing stream, suppresses the formation of dinitrile by-products under the then-current process conditions. From a practical perspective, adding too much Brønsted acid can catalyze other undesirable side reactions, and (in the presence of water at the appropriate process conditions) corrode process equipment. Thus the term "effective amount" has an upper limit for avoiding undesired side reactions and triggering higher-than-desired corrosion rates. The term "effective amount" as used herein is preferably defined as from 5 to 5,000 ppm by weight, based on the total weight of the composition comprising the dinitrile and the Brønsted acid. Preferably, the term "effective amount" is defined as from 5 to 1,000 ppm by weight, 10 to 500 ppm by weight, 50 to 400 ppm by weight, or 100 to 250 ppm by weight based on the total weight of the composition comprising the dinitrile and the Brønsted acid.

In a further aspect, the disclosure provides the use of a Brønsted acid to inhibit the formation of by-products from dinitrile compounds. In particular, the disclosure provides the use of a Brønsted acid to inhibit the formation of by-products during the distillation of dinitrile compounds.

In accordance with this aspect of the disclosure, the dinitrile is preferably selected from dinitrile compounds of the formula (I) as defined above. Preferably, the dinitrile is ADN and the Brønsted acid is used to inhibit the formation of CPI from the ADN, for example during the distillation an ADN-containing feedstream.

Optionally, the dinitrile comprises a Lewis acid. Suitable Lewis acids may be selected from $ZnX_2$, $BX_3$ and $AlX_3$, wherein X represents a halogen, trifluoromethanesulfonate, methanesulfonate or toluenesulfonate. In particular, the Lewis acid may be selected from $ZnCl_2$, $BCl_3$ or $AlCl_3$. The amount of Lewis acid present may suitably be in the range of from 50 to 10,000 ppm (by weight) based on the total weight of the dinitrile-containing feedstream, for example, the amount of Lewis acid present may be from 100 to 5,000 ppm, from 200 to 2,000 ppm, from 200 to 1,500 ppm or from 300 to 1,000 ppm based on the total weight of the dinitrile-containing feedstream.

The Brønsted acid may be used to inhibit the formation of by-products during the distillation of a reaction effluent from a process for the production of dinitriles via the hydrocyanation of unsaturated mononitriles. In particular, the Brønsted acid may be used to inhibit the formation of CPI during the distillation of a reaction effluent from a process from the production of ADN via the hydrocyanation of 3PN. The reaction effluent may comprise a Lewis acid as described above and/or a hydrocyanation catalyst, such as a nickel (0) catalyst stabilized with phosphorus-containing ligands (such as mono- or bi-dentate phosphite ligands) and/or excess phosphorus-containing ligands. Suitably, the Lewis acid, hydrocyanation catalyst, and any excess phosphorus-containing ligands are recovered from the distillation in a bottoms stream, preferably that also comprises the Brønsted acid.

Suitable Brønsted acids and amounts thereof in accordance with this aspect of the disclosure are as described above with reference to the first and second aspects of the disclosure. Where the use of a Brønsted acid comprises the distillation of a dinitrile-containing feedstream, suitable distillation conditions are as defined above. The distillation apparatus may comprise a single distillation column or a plurality of distillation columns. In the case that the distillation apparatus comprises a plurality of distillation columns, the Brønsted acid is supplied to at least one of the distillation columns. More preferably, the Brønsted acid is supplied to each of the distillation columns.

The operating mode of distillation apparatus can be batch, semi-batch or continuous. Further, the distillation apparatus may include, but not limited to, structured packing, random packing, tray sections, divided wall sections or combinations thereof. The distillation apparatus may also include inter-stage pump-arounds, overhead condensers, trim heaters, bottom reboilers, or combinations thereof.

EXAMPLES

Figure 1:
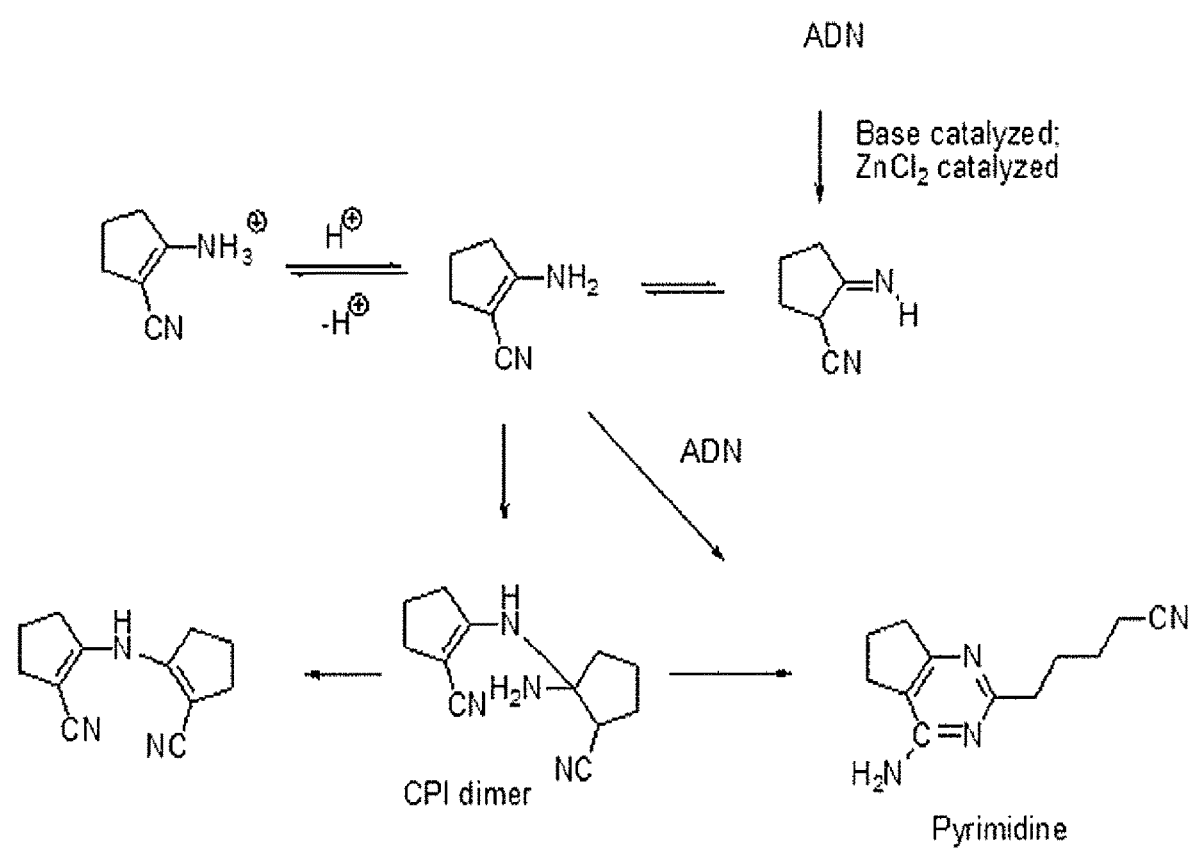
FIG. 1 is a simplified theoretical mechanism illustrating formation of CPI from ADN, and subsequent reactions. The mechanism is presented for illustration only, and is not intended to limit the scope of the disclosure which is defined by the claims.
Figure 2:
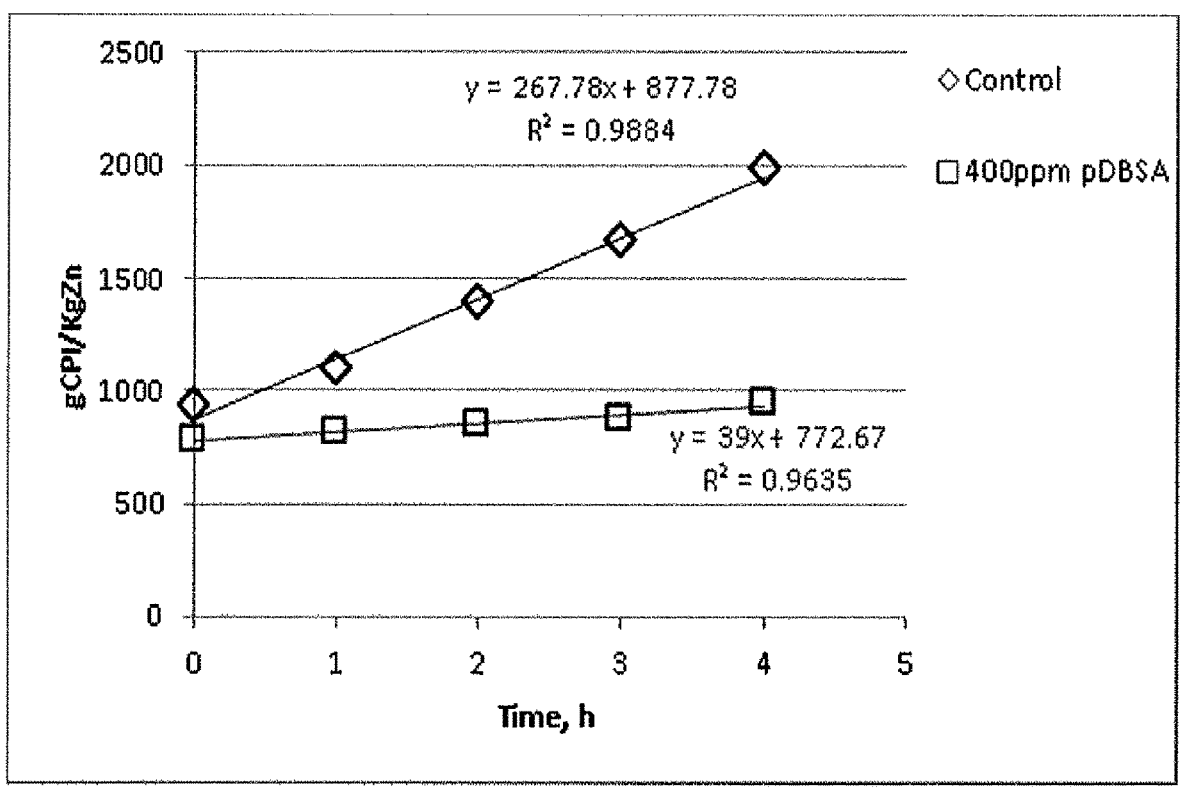
FIG. 2 graphically shows the results of the Examples, in which the addition of an alkyl benzene sulfonic acid decreased formation of CPI.

The following Examples demonstrate the disclosed method and its capability for use. The disclosed method is capable of other and different embodiments, and its several details are capable of modifications in various apparent respects, without departing from the spirit and scope of the present disclosure. Accordingly, the Examples are to be regarded as illustrative in nature and non-limiting. All parts and percentages are by weight unless otherwise indicated.

Example 1

To a three-neck 100 mL round bottom flask equipped with an overhead condenser, supplied nitrogen, magnetic stirbar, digital stir plate, and a heating mantle was charged refined adiponitrile (25 grams). The material was heated to 180° C., samples were taken every hour for 4 hours, and analysis was performed by gas chromatography.

Example 2

Example 1 was repeated, but zinc chloride (0.6 grams) was included.

Example 3

Example 2 was repeated, but para-dodecylbenzenesulfonic acid (1.58 grams) was included.

Example 4

Example 1 was repeated, but crude adiponitrile was used in place of refined adiponitrile, and the reaction temperature was 202° C. The composition of the crude adiponitrile was approximately: adiponitrile 95.4%, 2-methylglutaronitrile 3.8%, 2-ethylsuccinonitrile 0.4%, pentenenitriles 0.1%, and zinc 350 ppm.

Example 5

Example 4 was repeated, but phosphoric acid, >85% (0.05 grams) was included.

Example 6

Example 4 was repeated, but phosphoric acid, >85% (0.02 grams) was included.

Example 7

Example 4 was repeated, but para-dodecylbenzenesulfonic acid (0.01 grams) was included.

Example 8

Example 4 was repeated, but pyrophosphoric acid, 90% (0.01 grams) was included.

Example 9

Example 4 was repeated, but para-dodecylbenzenesulfonic acid (0.0044 grams) was included.

Example 10

Example 4 was repeated, but polyphosphoric acid (0.01 grams) was included.

Example 11

Example 4 was repeated, but phosphoric acid (0.0025 grams) was included.

TABLE 1

| Example | Adiponitrile | Additive | Conc., ppm | Temp, °C. | initial CPI, ppm | final CPI, ppm |
|---|---|---|---|---|---|---|
| 1 | refined | None | 0 | 180 | 13 | 17 |
| 2 | refined + added $ZnCl_2$ | None | 0 | 180 | 13 | 1522 |
| 3 | refined + added $ZnCl_2$ | pDBSA | 63200 | 180 | 13 | 202 |
| 4 | crude | None | 0 | 202 | 252 | 537 |
| 5 | crude | $H_3PO_4$ | 2000 | 202 | 124 | 31 |
| 6 | crude | $H_3PO_4$ | 800 | 202 | 143 | 60 |
| 7 | crude | pDBSA | 400 | 202 | 233 | 283 |
| 8 | crude | $H_4P_2O_7$ | 400 | 202 | 213 | 152 |
| 9 | crude | pDBSA | 176 | 202 | 269 | 400 |
| 10 | crude | PPA | 400 | 202 | 277 | 397 |
| 11 | crude | $H_3PO_4$ | 100 | 202 | 249 | 287 |

CPI = 2-cyanocyclopentylideneimine
Refined adiponitrile = refined adiponitrile, product of INVISTA.
Crude adiponitrile = unrefined adiponitrile
$H_3PO_4$ = Phosphoric acid, ≥85%, product of Sigma Aldrich.
$H_4P_2O_7$ = Pyrophosphoric acid, 90%, product of Sigma Aldrich.
pDBSA = para-dodecylbenzenesulfonic acid, product of Stepan Company.
PPA = polyphosphoric acid, 115% (based on $H_3PO_4$), product of Sigma Aldrich.

The data presented in Table 1 show the effectiveness of various additives on the formation of CPI during the refining of adiponitrile. The data show that acidic additives inhibit CPI formation. Comparison of examples 1-3 shows that the presence of $ZnCl_2$ increases the formation of CPI, but that the presence of the additive suppresses CPI formation. Comparison of examples 5-11 with example 4 demonstrate the effectiveness of various Brønsted acids for reducing CPI formation.

Example 12 demonstrates the present disclosure and its capability for use in reducing the formation of CPI during the continuous refining of adiponitrile.

Example 12

Phosphoric acid (84%) was added continuously to the feed of an adiponitrile distillation process to achieve a concentration of phosphoric acid delivered to the column in the feed, and the formation rate of CPI across the refining process was measured. The distillation was carried out in a column having 8 theoretical trays operating at an overhead temperature of 150° C., a reflux ratio of 0.5, with saturated liquid feed flowing to stage 2, counting the reboiler as the first stage.

Figure 3:
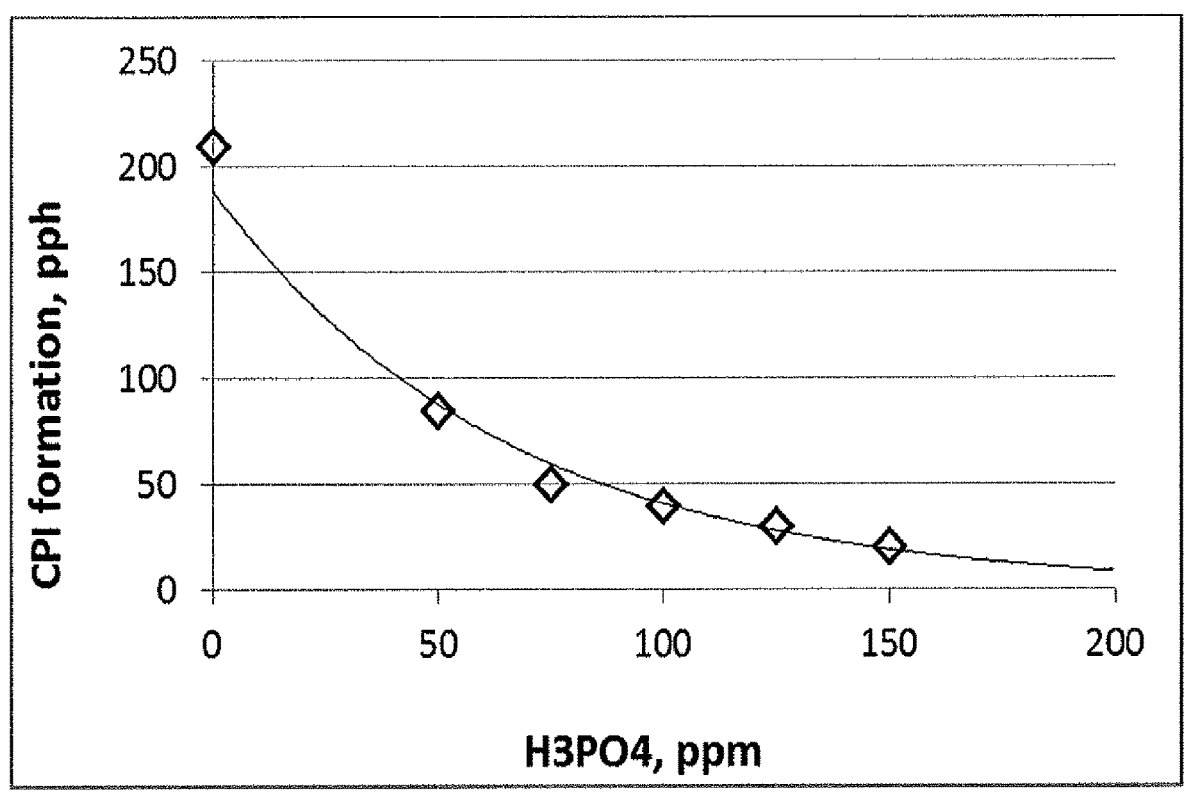
FIG. 3 graphically shows the results of Example 12, in which the addition of phosphoric acid decreased formation rate of CPI in a continuous process for refining adiponitrile by distillation as a function of the amount of phosphoric acid added.

Data are presented in Table 2, and FIG. 3. In Table 2 and FIG. 3, the phosphoric acid concentration (in ppm by weight) is measured in the feed to adiponitrile distillation process.

TABLE 2

| Phosphoric acid, ppm | CPI generation rate, kg per hour | CPI generation rate, pph |
|---|---|---|
| 0 | 95.3 | 210 |
| 50 | 38.6 | 85 |
| 75 | 22.7 | 50 |
| 100 | 18.1 | 40 |
| 125 | 13.6 | 30 |
| 150 | 9.1 | 20 | pph = pounds of CPI generated per hour

While the illustrative embodiments of the disclosure have been described with particularity, it will be understood that various other modifications will be apparent to and may be readily made by those skilled in the art without departing from the spirit and scope of the disclosure. Accordingly, it is not intended that the scope of the claims hereof be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The invention claimed is:

1. A method of refining a dinitrile compound by distillation, the method comprising:
   (a) supplying (i) a feedstream comprising the dinitrile compound, wherein the dinitrile compound is adiponitrile and wherein the feedstream comprises a Lewis acid that is $ZnX_2$, $BX_3$, or $AlX_3$, wherein X represents a halogen, trifluoromethanesulfonate, methanesulfonate, or toluenesulfonate, and (ii) a Brønsted acid to a distillation apparatus, wherein
   the Brønsted acid is supplied to the distillation apparatus in an amount of from 5 to 5,000 ppm by weight, based on the total weight of the dinitrile-containing feedstream and the Brønsted acid,
   the amount of the Brønsted acid supplied to the distillation apparatus is effective to inhibit the formation of 2-cyanocyclopentlideneimine (CPI) from the dinitrile compound in the distillation apparatus, and
   the Brønsted acid does not degrade in the distillation apparatus; and
   (b) withdrawing from the distillation apparatus an overhead distillate stream comprising the dinitrile compound and withdrawing the Brønsted acid from the distillation apparatus in a bottoms stream comprising the Brønsted acid.

2. A method according to claim 1, wherein the amount of Lewis acid present in the dinitrile-containing feedstream is in the range of from 50 to 10,000 ppm by weight based on the total weight of the dinitrile-containing feedstream.

3. A method according to claim 1, wherein the feedstream to the distillation apparatus in (a) comprises a reaction effluent from a process for the production of dinitriles via the hydrocyanation of unsaturated mononitriles.

4. A method according to claim 3, wherein the feedstream to the distillation apparatus in (a) comprises a reaction effluent from a process for the production of ADN via the hydrocyanation of 3PN.

5. A method according to claim 4 wherein the reaction effluent comprises a nickel (0) catalyst stabilized with phosphorus-containing ligands and/or excess phosphorus-containing ligands.

6. A method according to claim 1, wherein the Brønsted acid is selected from phosphoric acids, sulfuric acid, $C_4$ to $C_{12}$ alkanesulfonic acids and $C_7$ to $C_{18}$ alkylbenzenesulfonic acids.

7. A method according to claim 6, wherein the Brønsted acid is selected from phosphoric acid, polyphosphoric acid, pyrophosphoric acid, octanesulfonic acid, decanesulfonic acid, dodecanesulfonic acid, 4-toluenesulfonic acid, 4-ethylbenzenesulfonic acid, 4-butylbenzenesulfonic acid and 4-dodecylbenzenesulfonic acid.

8. A method according to claim 1, wherein the distillation apparatus is operated with a bottoms temperature in the range of from 150 to 200° C.

9. A method according to claim 1, wherein the distillation apparatus comprises a plurality of distillation columns and wherein the Brønsted acid is supplied to at least one of the distillation columns.

10. A method for inhibiting the formation of by-products from a dinitrile compound, the method comprising adding from 5 to 5,000 ppm by weight of a Brønsted acid to a composition comprising the dinitrile compound, based on the total weight of the dinitrile-containing composition and the Brønsted acid, wherein the dinitrile compound is adiponitrile, the composition comprises a Lewis acid that is $ZnX_2$, $BX_3$, or $AlX_3$, wherein X represents a halogen, trifluoromethanesulfonate, methanesulfonate, or toluenesulfonate, the amount of the Brønsted acid supplied to the composition is effective to inhibit the formation of 2-cyanocyclopentylideneimine (CPI) from the dinitrile compound, and wherein the Brønsted acid has lower volatility than the dinitrile compound and the Brønsted acid does not degrade in the composition.

11. A method according to claim 10, for inhibiting the formation of CPI from ADN.

12. A method according to claim 10, comprising refining the dinitrile compound by distillation, wherein (i) a feedstream comprising the dinitrile compound and (ii) the Brønsted acid are supplied to a distillation apparatus; an overhead distillate stream comprising the dinitrile compound is withdrawn from the distillation apparatus; and the Brønsted acid is withdrawn from the distillation apparatus in a bottoms stream comprising the Brønsted acid; wherein the amount of the Brønsted acid supplied to the distillation apparatus is effective to inhibit the formation of 2-cyanocyclopentylideneimine (CPI) from the dinitrile compound in the distillation apparatus.

13. A method according to claim 10, wherein the method comprises adding 5 to 800 ppm by weight of the Brønsted acid to the composition comprising the dinitrile compound based on the total weight of the composition comprising the dinitrile compound and the Brønsted acid.

* * * * *